(12) United States Patent
Dworkin

(10) Patent No.: US 6,613,001 B1
(45) Date of Patent: Sep. 2, 2003

(54) INTRAORAL APPLIANCE, MONITORING DEVICE AND METHOD OF TREATING PATIENT

(76) Inventor: Jeffrey B. Dworkin, 2500 Edgehill Rd., Cleveland Heights, OH (US) 44106

( * ) Notice: Subject to any disclaimer, the term of this patent is extended or adjusted under 35 U.S.C. 154(b) by 15 days.

(21) Appl. No.: 09/638,559

(22) Filed: Aug. 14, 2000

(51) Int. Cl.[7] .......................... A61B 5/103; A61B 5/117
(52) U.S. Cl. ...................................................... 600/590
(58) Field of Search ................................ 600/590, 587; 433/71, 68, 6, 24, 215; 128/776, 777, 897, 898; 340/573.1

(56) References Cited

U.S. PATENT DOCUMENTS

| | | |
|---|---|---|
| 2,604,559 A | 7/1952 | Shapiro |
| 3,259,129 A | 7/1966 | Tepper |
| 3,297,021 A | 1/1967 | Davis et al. |
| 3,390,459 A | 7/1968 | Seidenberg |
| 3,608,541 A | 9/1971 | Hall |
| 3,822,694 A | 7/1974 | Mills |
| 3,861,688 A | 1/1975 | Butler |
| 3,885,576 A | 5/1975 | Symmes |
| 3,929,335 A | 12/1975 | Malick |
| 3,974,491 A | 8/1976 | Sipe |
| 3,983,865 A | 10/1976 | Shepard |
| 4,007,733 A | 2/1977 | Celeste et al. |
| 4,055,168 A | 10/1977 | Miller et al. |
| 4,149,445 A | 4/1979 | Wis |
| 4,178,589 A | 12/1979 | Nunn et al. |
| 4,191,949 A | 3/1980 | Myers |
| 4,198,990 A | 4/1980 | Higgins et al. |
| 4,258,709 A | 3/1981 | Flack et al. |
| 4,310,002 A | 1/1982 | Takinishi et al. |
| 4,330,276 A | 5/1982 | Becker et al. |
| 4,608,998 A | 9/1986 | Murdock |
| 4,617,525 A | 10/1986 | Lloyd |
| 4,629,424 A | 12/1986 | Lauks et al. |
| 4,647,918 A | 3/1987 | Goforth |
| 4,706,292 A | 11/1987 | Torgeson |
| 4,842,519 A * | 6/1989 | Dworkin ...................... 600/590 |
| 5,078,153 A * | 1/1992 | Nordlander et al. ......... 600/590 |
| 6,089,864 A * | 7/2000 | Buckner et al. ............... 433/71 |

FOREIGN PATENT DOCUMENTS

| | | | |
|---|---|---|---|
| DE | 40 03 947 A1 * | 8/1991 | ................. 600/590 |
| GB | 2 023 005 A | 5/1979 | |

OTHER PUBLICATIONS

Popular Mechanics, Jan. 1971, pp. 94 & 95.

* cited by examiner

Primary Examiner—Max F. Hindenburg
Assistant Examiner—Brian Szmal
(74) Attorney, Agent, or Firm—Renner, Otto, Boisselle & Sklar, LLP

(57) ABSTRACT

An intraoral device makes a new treatment of dental problems possible. The device includes electronic circuitry, including a proximity detector, a variable time delay, a signal generator and a power supply, to sense and record the frequency and duration of unwanted or undesirable relative positions of body parts within the oral cavity. The recorded data stored by the circuitry enables a dentist to chart the progress of a patient during treatment and diagnose whether functional problems exist which require a specific treatment plan. The undesirable position may be teeth clenched, jaw open with teeth unclenched, tongue pressed against the teeth or a retruded portion of the lower jaw. When these positions have been assumed for too long, a signal reminds the patient. This automatic signal makes it possible for the patient to unlearn bad habits or learn new habits.

31 Claims, 4 Drawing Sheets

INTRAORAL APPLIANCE, MONITORING DEVICE AND METHOD OF TREATING PATIENT

FIELD OF THE INVENTION

The present invention relates generally to dentistry and specifically to a method, apparatus and monitoring device for the treatment of various problems related to improper use of jaw musculature and/or to monitor a patient's compliance with his or her treatment regimen.

BACKGROUND OF THE INVENTION

There are numerous dental problems that arise from improper use of jaw musculature. One of these is clenching, a condition in which a patient constantly or excessively presses his or her teeth against each other. Clenching can cause excessive wear of the teeth, headaches, and fatigue and soreness of the jaw muscles.

There are at least three schools of thought on the treatment of clenching. One traditional treatment involves placing a protective layer of acrylic material (called a splint) over the involved teeth. This acrylic layer serves to protect the teeth from direct contact, thus reducing wear, and to spread the load caused by clenching so that it is shared more equally among the neighboring teeth. This reduces wear of the teeth, but the acrylic protective layer does not address the problem of clenching, which frequently continues indefinitely. This forces the patient to wear the splint indefinitely. In some cases the urge to clench is worsened.

A second traditional treatment for clenching is occlusal adjustment. This treatment involves selective grinding of teeth so that the load on the teeth caused by clenching is carried evenly by several teeth rather than being concentrated on one or two. This technique is successful with some but not all types of clenching.

A third school of thought is that there is nothing that can be done about clenching. This approach may have heretofore had the advantage of candor, but it left patients with unnecessary discomfort. Muscle relaxants are often prescribed in these instances. This group of drugs may adversely effect performance, and therefore can in some instances only be used when the patient is at home.

A second class of dental problems relates to what are termed problems in the vertical frame of reference. Examples of these problems are: (1) Dental open bite which is characterized by contact between the posterior teeth without contact between the front teeth when the jaw is closed; (2) skeletal open bite which is characterized by a sloping mandibular plane and a long face; and (3) skeletal deep bite which is characterized by short faces and mandibular planes that are nearly horizontal or parallel with the floor. Skeletal deep bite patients also have dental deep bite which is characterized by excessive overlap of the front teeth. Treatments for problems of this type are discussed below.

One method of treating a dental open bite is to mount ceramic magnets on the rearmost molars with like poles facing each other so that the molars are slowly forced more deeply into the bone which supports them. A disadvantage to this method is that the magnets and their acrylic housing force the jaw open 5–6 millimeters in the rear and perhaps twice that at the front. This forces the patient to walk around with his or her mouth open, which is embarrassing and uncomfortable. Patients also have difficulty keeping their jaws in such a position that the repelling magnets are directly opposing one another. Thus, there is a tendency for the lower jaw to slide from side to side and not to stay centered. As a result, these patients are frequently asked to wear a chin strap and headgear apparatus to center the lower jaw. This method of treating open bites is prone to the problem of lack of patient cooperation.

Another problem associated with dental open bites is called tongue thrusting. A patient with this problem habitually presses his or her tongue forward against his or her front teeth. This problem can be addressed by placing a cage directly behind the upper or lower front teeth. This appliance restrains the tongue from coming forward where it has forced the front teeth apart. The patient is instructed to keep the tongue behind the cage without touching it and to move the tongue backward, away from the cage whenever it touches the cage. The problem with this appliance is that patients forget to remind themselves to move their tongues backward, and they rest their tongues against the cage. When the appliance comes off, the tongue frequently comes forward to rest against the front teeth again. Relapses frequently occur.

When dental open bites are present in patients in their teens, or later as an adult, the treatments for dental open bite are orthodontic treatment in combination with extractions of permanent teeth, or orthodontic treatment in combination with surgery, which usually includes extraction of permanent teeth.

Skeletal open bites are traditionally treated by orthodontists through the use of orthodontics, possibly including the extraction of teeth, and using orthopedic force in the form of headgear which imposes an intrusive force to the maxilla and maxillary teeth. Extractions help to solve the problem in a minor way and require the removal of four perfectly good teeth. The successful use of headgear is dependent upon the cooperation of the patient. The headgear includes a brace that circumscribes the head and neck, and it is cumbersome and uncomfortable. Experience has shown that cooperation in wearing the headgear is often less than complete. The use of extractions and headgear treat only the symptoms of skeletal open bites. The underlying cause of the problem which is the lack of sustained contact between the teeth is not addressed by this treatment.

Dental and skeletal deep bite are treated by orthodontists through the use of an orthodontic regimen which often includes propping the front teeth open with an acrylic bite plane. This leaves the posterior teeth apart and allows them to erupt into contact with each other. In the short run this treatment appears to be stable, but after about a year the deep bite may begin to return because the underlying cause of the problem (chronic clenching of teeth) was never addressed.

Another class of dental problems relates to what is termed problems in the horizontal frame of reference. Mandibular retrognathia is one such problem. It is characterized by the lower jaw being positioned too far behind the upper jaw in the horizontal frame of reference. This condition is conventionally treated with bulky acrylic appliances which hold the lower jaw forward and restrain the lower jaw from moving backward. These appliances have been shown to create undesirable side effects related to this restraint such as proclination of the lower anterior teeth. Other treatments have been: Orthodontics that usually includes extraction of teeth, or orthodontics that utilize orthopedic forces to push the upper jaw backward to meet the lower jaw. If the problem of mandibular retrognathia has not been treated by 12 to 14 years of age, it is often necessary to treat the problem with orthodontics in combination with surgery that is designed to bring the lower jaw forward.

Other classes of dental problems arise when patients fail to wear their dental splint, retainer or other corrective dental hardware. Patients, especially younger patients, routinely hinder their treatment program by failing to wear the prescribed dental hardware. When asked, most patients will not confess to the failure to wear their prescribed dental hardware. Accordingly, there is a need for an appliance which can monitor whether a patient is in compliance with his or her prescribed hardware regimen.

SUMMARY OF THE INVENTION

The present invention provides a new approach to treating and monitoring the dental problems discussed above. The present invention can remind the patient of unconscious, undesirable behavior every time it occurs and can help the patient to learn new habits. In addition, the present invention permits a patient's treating dentist or orthodontist to monitor the patient's progress through each patient's prescribed treatment regimen. This is accomplished by the use of electronic circuitry attached to, e.g., the upper teeth which senses the proximity of the lower teeth and signals the patient when the jaw is in an undesirable position. The circuitry also contains a memory and readout apparatus. The memory and readout apparatus may permit a treating dentist or orthodontist to monitor the amount of time and number of times bite forces exceed a predetermined threshold. In addition, the memory and readout apparatus may permit the monitoring of jaw positions by recording the amount of time the teeth are more than a predetermined distance apart, the amount of time the teeth are together and/or the number of times biting occurs.

For patients who clench, the circuitry may sense a closed jaw, and when the jaw has been held closed too long, e.g., 3 or 5 seconds, a signal (be it audible or otherwise) is generated alerting the patient to relax his or her jaw muscles by opening the jaw. Conversely, with open bite patients the circuitry may be arranged to signal and monitor the patient when the jaw has been open too long. Additionally or alternatively the present invention may signal and monitor the patient when his or her tongue is being pressed against the back sides of the front teeth. By providing a signal to the patient at the appropriate time, the patient can modify his or her behavior so that the cause of the patient's problem can be treated: Clenchers learn to relax their jaw muscles; open bite patients strengthen their jaw muscles; and tongue thrusters learn not to press against their teeth. By monitoring the above conditions the present invention permits a dentist or orthodontist to have an objective means of monitoring and diagnosing the progress (or lack thereof) a patient is making progress in their treatment regimen.

This invention may also be adapted to create habits that are lacking by reminding the patient when the desired habit or function is not being practiced. Examples of this application are in the treatment of skeletal open bite or mandibular retrognathia. In skeletal open bite patients there is thought to exist a lack of sustained contact between upper and lower jaws. This results in the tendency for the face to grow downward instead of forward. The result is these patients have extremely long faces. By using the present invention to sense the lack of contact between teeth, the patients can be trained to keep their teeth in contact during certain periods during the day. This stops or reverses the downward growth and at the same time trains the muscles to keep the lower jaw in more frequent contact with the upper jaw. Additionally, the above device can be configured to permit it use in training mandibular retrognathia patients to hold their jaws forward in the correct lower jaw position.

The present invention includes an electronic circuit which may comprise a reed switch, time delay, oscillator, signal generator (e.g., a sound production or light emitting device), memory component, readout device and power supply all encapsulated in suitable plastic material (e.g., an acrylic or a watertight synthetic resin) and mounted to a molar, usually a maxillary molar. To treat clenching or open bite problems the opposing molar carries a small magnet to actuate the reed switch. The device is removably mounted to a band surrounding the tooth so that it may readily be removed for repair or when it is not desirable to have it operating. With regard to the readout device, it can be integrated into the device as mounted in the patient's mouth thereby permitting the doctor to directly monitor the patient's progress during an office visits. In another embodiment, the device can be set up to include an integrated readout device so as to permit the patient to monitor his or her own progress between office visits.

In one embodiment, the device can have connectors which permit a treating dentist or orthodontist to attach a readout device to display the information contained within the device's memory. In another embodiment, the device can include circuitry which can produce a series of audible beeps which are coded to represent the data contained in the device's memory. These beeps can be recorded by a device outside the patient's mouth and then translated to yield the data contained within the device's memory.

In another embodiment, the device can contain circuitry which generates a signal comprising a slight vibration (similar in nature to that of a pager). Such a vibrational mode is advantageous in that it is quite and does not interrupt other individuals in the immediate vicinity of the patient. In another embodiment, the device can contain a means to permit switching between an audible mode and a vibrational mode.

To treat tongue thrusting, a cage is mounted just behind the upper front teeth. The cage is movable and spring biased rearwardly to a position slightly spaced from the upper front teeth. When the tongue is pressed against the cage, the cage moves forward. A magnet is mounted to the cage, and when the cage moves, the magnet actuates the circuitry to alert the patient. The tongue thrusting treating device is mounted by means of a pair of polymeric splints which surround the three or four rearmost maxillary teeth on each side and in one of which the circuitry is embedded. The splints are connected by thick wires or bars which are contoured to follow the roof of the mouth. Because tongue thrusting is often accompanied by an open bite, additional circuitry which can be arranged to detect an open bite may also be embedded in one of the polymeric splints. The monitoring function of the present invention enables a treating dentist or orthodontist to monitor the number of times and/or amount of time the tongue is thrust forward.

The invention may also be adapted to be incorporated into a retainer or other corrective dental device. In such a situation the monitoring function of the present invention permits a treating dentist or orthodontist to monitor the amount of time the corrective hardware has spent at or above a certain temperature. This enables the treating dentist or orthodontist to ascertain whether such corrective dental appliances have been worn as prescribed.

DETAILED DESCRIPTION OF THE INVENTION

Figure 1:
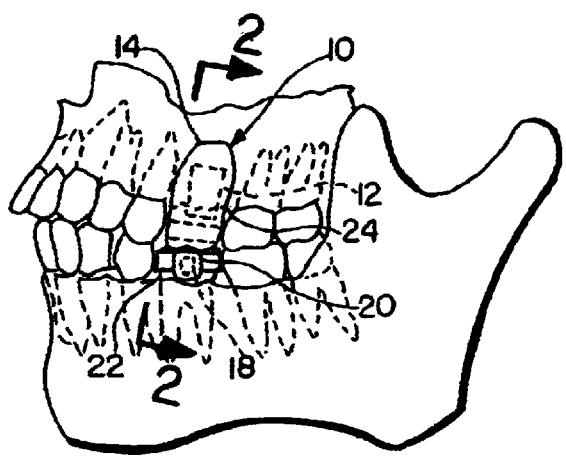
FIG. 1 is a side skeletal view showing one embodiment of an intraoral appliance constructed in accordance with the present invention.
Figure 2:
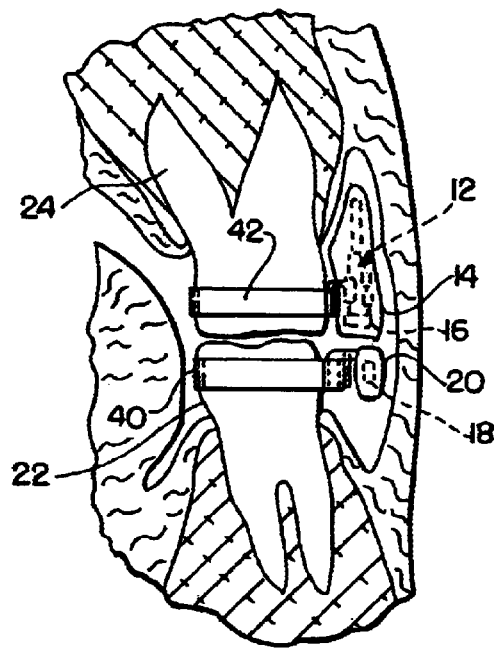
FIG. 2 is a view looking generally in the direction of arrows 2—2 of FIG. 1 but further showing the soft tissues including cheek, tongue, gums and roof of the mouth.

The intraoral appliance 10 illustrated in FIGS. 1 and 2 includes an electronic signaling circuit 12 embedded in an polymeric housing 14 (e.g., an acrylic or a watertight synthetic resin). The circuit 12, which will be described in greater detail below, includes a detector for sensing the relative position of body parts within the oral cavity. In the embodiment illustrated in FIGS. 1 and 2, proximity of the first mandibular molar 22 to the first maxillary molar 24 is sensed by means of a reed switch 16 mounted within the polymeric housing 14 and a magnet 18 embedded in another polymeric housing 20 mounted to the mandibular molar 22. The polymeric housings 14 and 20 are molded to conform to the particular patient's morphology, and the circuitry is extremely compact so that the resulting apparatus may be worn without discomfort and discreetly.

Where the intraoral appliance 10 is used for the treatment of clenching, the circuitry 12 is configured so that when the mandibular and maxillary molars 22 and 24 are in contact, the reed switch 16 is closed. When the teeth 22 and 24 remain in contact for more than a predetermined length of time (in one embodiment any where from about one to about twenty seconds), a signal is generated which is audible or vibratory to the patient in whose mouth the appliance is installed. By being reminded that his or her jaw is clenched, the patient can break this bad habit and thus alleviate the symptoms it causes. In addition, the intraoral appliance may also contain a clock and counter memories and readout device for monitoring and displaying the position of the upper and lower jaws and the duration that the jaws are clenched, as is discussed below.

Figure 3A:
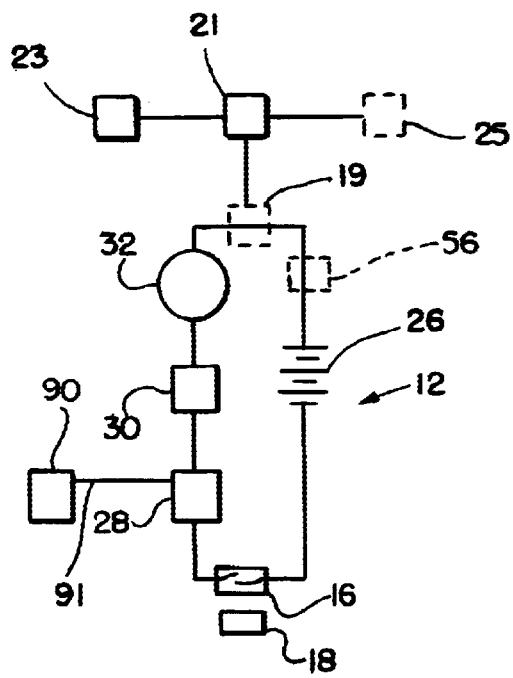
FIG. 3A is a schematic illustration of one embodiment of a circuit utilized in the present invention.

The circuit 12 includes a detector for detecting the proximity of body parts. In the embodiment of the invention illustrated in FIGS. 1 and 2 the detector comprises the reed switch 16 which is closed by a magnet 18 (FIG. 3A). When the reed switch 16 is closed, power from a battery 26 flows through a time delay circuit 28, and after a predetermined length of time (this time being adjustable), power is then passed to an oscillator 30 and from the oscillator 30 to a piezoelectric transducer 32 to alert the patient that he or she is clenching and has been clenching for too long.

Figure 10:
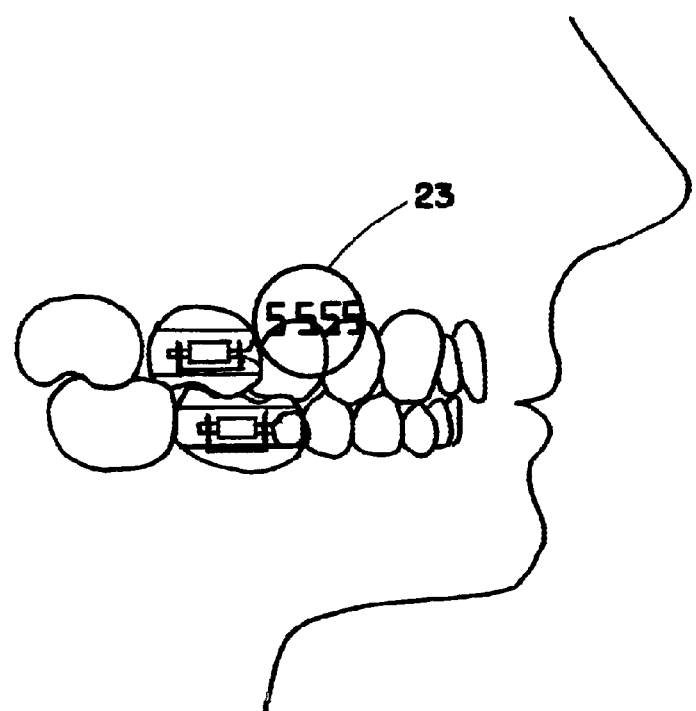
FIG. 10 is a view showing another embodiment of a device for monitoring certain conditions in patients win which a readout unit is separate from a monitoring device and circuitry.

In addition, the circuit 12 includes clock memory 19, which records the duration of any number of occurrences, a counter memory 21, which records, for example, the number of times that the upper and lower jaws are clenched, and a readout 23. If the device is only being used at night, the memories 19 and 21 can be permanently and directly connected to the readout 23. Alternatively, the readout 23 can be detachable and is activated when brought into contact with connectors on the circuit 12 (FIG. 10). In another embodiment, the readout 23 can contain additional memory for storing data beyond that of memories 19 and 21.

Still another alternative for the readout is that readout 23 receives signals from the piezoelectric transducer 32 and generates a series of tones based upon information stored in the memory sections of circuit 12 (e.g., the clock memory 19 and the counter memory 21). These tones would be emitted from circuit 12 when the circuit is prompted. For example, after having removed the intraoral appliance 10 from a patient's mouth the intraoral appliance 10 could be plugged into a receptacle and activated by another reed switch. The receptacle can in turn be connected to a computer (e.g., a standard desktop or laptop computer) through the computer's sound card. The computer, through the use of appropriate software, would interpret the sound data generated by circuit 12 of the intraoral appliance 10 and display on the computer's display the data stored in circuit 12's memories (e.g., the duration of any number of occurrences and the number of times that the upper and lower jaws are clenched).

In yet another embodiment, the readout 23 can be replaced by a small speaker which contains therein the necessary circuitry to generate a series of audible beeps. When activated as described above or by an appropriate command (e.g., an audible command when a microphone and the necessary circuitry is included in the device), the speaker will generate a series of tones or beeps based upon information stored in the memory sections of circuit 12 or the memory section, if any, of the speaker portion of the device. These tones can either be communicated to a computer as described above or can be recorded using another device (e.g., a tape recorder) and interpreted by any suitable means (such as a computer program).

In one embodiment, the readout 23 will be a conventional LCD display with its own power supply which is placed inside the polymeric housing 14. All of these circuit elements are conventional. It is contemplated that in practice the circuit elements 19, 21, 28 and 30 will be formed in a single integrated circuit.

The strength of the magnetic field surrounding the magnet 18 and its position relative to the reed switch 16 determines when the reed switch will close for treating clenching and cause a clenching incident to be recorded in the counter memory 21 and the time duration of clenching in the clock memory 19. The magnet 18 should be positioned so that when the teeth 22 and 24 come into contact the magnetic field at the reed switch 16 is just sufficient to close the switch. This is accomplished either by proper selection of the magnet's size or field strength or by positioning the magnet 18 relative to the reed switch 16.

In one embodiment, for treatments which involve teaching the patient to hold his or her jaw closed, the magnet 18 might be such as to actuate the reed switch 16 when teeth 22 and 24 are close to each other but not yet touching. For such treatments, the clock memory 19 and the counter memory 21 record the amount of time when teeth 22 and 24 are in contact with one another and/or the amount of time when teeth 22 and 24 are more than a predetermined distance apart. Again the information stored in the memories 19 and 21 can be retrieved by either of the above described readout devices.

In another embodiment, the reed switch 16 is connected to different parts of the circuit 12 so as to work in a manner diametrically opposed to that of the clenching configuration. That is, the circuit 12 is set up in such a way as to produce a signal (as described above) when the patient opens his or her mouth for a predetermined, adjustable amount of time (e.g., about one to about 20 seconds). In another embodiment, this circuit can also prevent the patient from developing a clenching habit, in view of the prompting to keep their mouth closed, by the inclusion of additional circuitry which is similar in nature to the clenching configuration described above. That is, in one embodiment, the device contains both circuitry to prevent "slack jaw" and to prevent clenching. In this instance the device is adjusted so that the patient can neither clench for too long a period of time or have their mouth open for too long a period of time. In still another embodiment, the clenching portion of the device can be activated only during certain time periods throughout the day (e.g., at night).

The time delay circuit 28 provides an adjustable time delay of between approximately zero to twenty seconds. This delay allows the patient to talk, eat, and swallow, all of which require contact between mandibular and maxillary teeth. The length of the time delay may be made variable. This can be done in a number of ways. Either a potentiometer can be used so that the resistance in an R-C circuit may be varied, or electronic components (either resistors or capacitors) could be removed or added to the circuit to achieve the same result. The same result could be obtained digitally with a clock and counter. The length of time would be varied by varying the length of the count. Again, such a circuit is conventional.

As discussed above, proximity of the mandibular and maxillary teeth is sensed by means of the detector including the reed switch 16 and magnet 18. The detector could also be responsive to inductance or capacitance in which case a magnet would not be required but merely a piece of metal, stainless steel, for example. The important thing is not what type of proximity detector is used, but that it be capable of generating a signal when the body parts whose positions are to be detected come into a preselected spatial relation and of stopping the signal once the body parts move to a different position. Further, an advantage to the use of a reed switch/magnet and/or capacitance/inductance detector is that full freedom of movement of the mandible is maintained because there is no mechanical interconnection between the body parts whose position is being detected.

Figure 4:
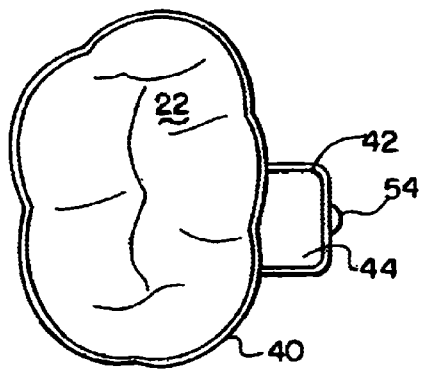
FIG. 4 is a plan view showing a tooth with a band around the tooth for securing an apparatus which forms a part of the present invention.
Figure 5:
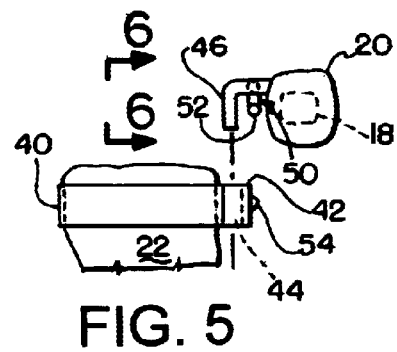
FIG. 5 is an elevation view of the tooth of FIG. 4 with band attached and further showing another component of the present invention prior to installation.

The circuit 12 is embedded in an polymeric housing 14 (FIG. 2). Similarly, the magnet 18 is embedded in a second polymeric housing 20. Both of these housings are secured to their respective teeth by means of orthodontic bands 40, 42. The band 40 is illustrated in FIG. 4. It is formed of a conventional steel alloy which circumscribes the mandibular molar 22. A U-shaped band 42 extends from the buccal surface of the band 40 and is connected to it by, for example, welding. The loop 42 and band 40 together define an opening 44 which receives a pin 46 (FIG. 5) which extends from the polymeric housing 20.

Figure 6:
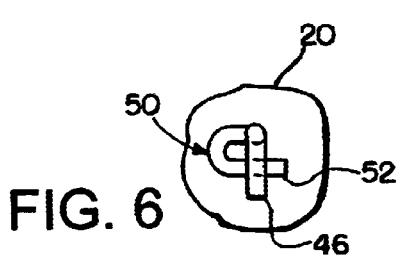
FIG. 6 is a view looking in the direction of arrows 6—6 of FIG. 5.

The pin 46 is L-shaped and projects laterally from the polymeric housing 20 and then downward, the downward leg being proportioned to fit in the opening 44. A U-shaped wire spring 50 is mounted to the horizontal leg of the pin 46. The wire spring 50 is mounted horizontally so that its lowermost leg 52 (FIGS. 5 and 6) is slightly above the bottom of the downward leg of pin 46. As the downward leg of pin 46 is inserted into the opening 44, the leg 52 of spring 50 encounters a dimple 54 which projects laterally from the outside surface of the loop 42. The spring 50 yields as the polymeric housing 20 is pushed downward, and ultimately the lowermost leg 52 of the spring snaps under the bottom side of the dimple 54 to hold the polymeric housing 20 firmly in place. There are times when a patient may choose not to have his intraoral appliance operative. In this case, the spring 50 may be easily manipulated to permit the downward leg of pin 46 to be withdrawn from the opening 44. A similar band and pin arrangement may be used to secure the circuit 12 and the polymeric housing 14 to the maxillary molar 24.

Alternatively, attachment means other than orthodontic bands can be used so long as the attachment means used provide secure and stable positioning of the polymeric housings.

The intraoral appliance 10 as illustrated in FIGS. 1–3A and 4–6 is configured for the treatment of clenching. Specifically, the circuitry is arranged to generate a signal when mandibular and maxillary molars have been in contact with each other for a period of time which exceeds that required for eating, talking or swallowing. By being reminded of the improper or undesirable action every time it occurs, the patient is able to break bad habits, in this case excessive clenching.

Figure 11:
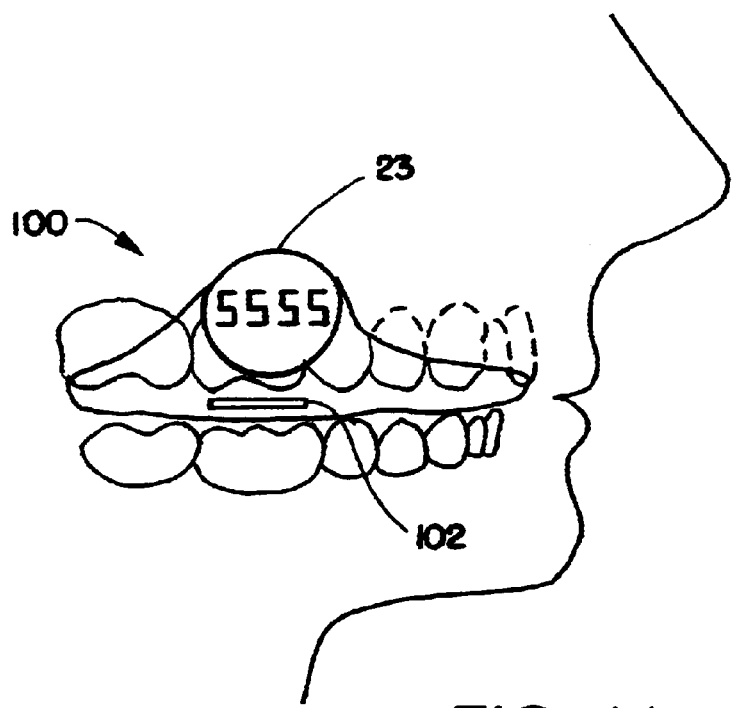
FIG. 11 is a view showing one embodiment of a device for monitoring certain conditions in patients in which a readout unit with the monitoring device and circuitry is integrated into an polymeric mouth piece.

In addition, the above described circuitry can be placed into a night guard or splint 100 which can also contain, embedded therein or hardwired thereto, the above described readout device 23 (FIG. 11) for displaying any recorded information. Such a night guard or splint 100 can optionally include a conductive rubber transducer 102 and a bite force memory 25 (FIG. 3A) similar to the clock and counter memories 19 and 21, respectively, as described above. The conductive rubber transducer 102 permits the treating dentist or orthodontist to monitor a patient's bite forces. The bite force memory 25 records bite forces that exceed a predetermined threshold. Whereas the clock and counter memories 19 and 21, respectively, record the amount of time and number of times such bite forces exceed the predetermined threshold. In the case of a patient with an open bite the clock and counter memories 19 and 21, respectively, record the amount of time and/or number of times the patient's teeth are out of contact by a predetermined distance.

The circuitry 12 may also be arranged to generate a signal when the opposite condition obtains. For a variety of reasons, including the treatment of an open bite, a patient might need to learn to keep the jaw muscles tense. In this case, rather than using a normally open reed switch 16, a normally closed reed switch is included in the circuit. The effect is that whenever the maxillary and mandibular teeth are out of contact for a length of time which exceeds a predetermined length of time, an audible signal is generated to alert the patient to close his mouth. To treat mandibular retrognathia, the circuitry 12 is arranged as for open bite treatment, but the magnet and reed switch are positioned so that the alarm is quiet only when the jaw is thrust forward. In such a situation the clock and counter memories 19 and 21, respectively, will record the amount and number of times the distance between the maxillary and mandibular teeth exceeds a predetermined distance, before, during and/or after treatment.

In another embodiment, the normally closed reed switch can be eliminated in favor of a different portion of the circuit 12 which is designed to function like a normally closed reed switch.

For treatment of mandibular retrognathia, open bite, or other condition where closing the jaw would help in treatment, circuitry arrangements are possible other than that discussed in the preceding paragraph. For example, a normally open reed switch could be used together with a circuit which will actuate the oscillator 30 when the reed switch has been open more than a predetermined length of time. Regardless of which arrangement is used, the patient receives an audible signal whenever his or her jaw has been too long in an undesirable position. Additionally, regardless of which arrangement is used, the clock and counter memories 19 and 21, respectively, record the amount and number of times the patient's maxillary and mandibular teeth are more than a predetermined distance apart. The recorded information is displayed either on a readout unit hardwired to the circuitry 12 or a detachable readout unit or an audible readout unit, as described above.

For treatment of open bite problems, the circuit 12 illustrated in FIG. 3A includes an additional timer circuit 56 in series with the other circuit elements. The timer circuit 56 is conventional and includes a twenty-four hour clock which is programmed to limit the number of hours or time periods that the circuit 12 operates in the course of a day. This permits the jaw muscles to relax and rest and prevents the creation of a clenching problem. For example, the timer circuit 56 may actuate the circuit 12 only between 7 p.m. and 11 p.m. and may be programmed so that during this four hour period it is on only for alternative 20 minute intervals. Later in treatment, the dentist may want to change the time range to 9 p.m. to 11 p.m., with the circuit on for alternate 15 minute intervals. Alternatively, the circuitry depicted in FIG. 3B (discussed more fully below)can be modified as described above to achieve the same results.

In a commercial device, it is contemplated that the timer circuit 56 is integrated into a single chip together with the other circuit elements. The timer circuit 56, as indicated, is adjustable to control when the circuit 12 is operative. Therefore, the timer circuit 56 may be helpful in the treatment of problems in addition to open bites.

Figure 7:
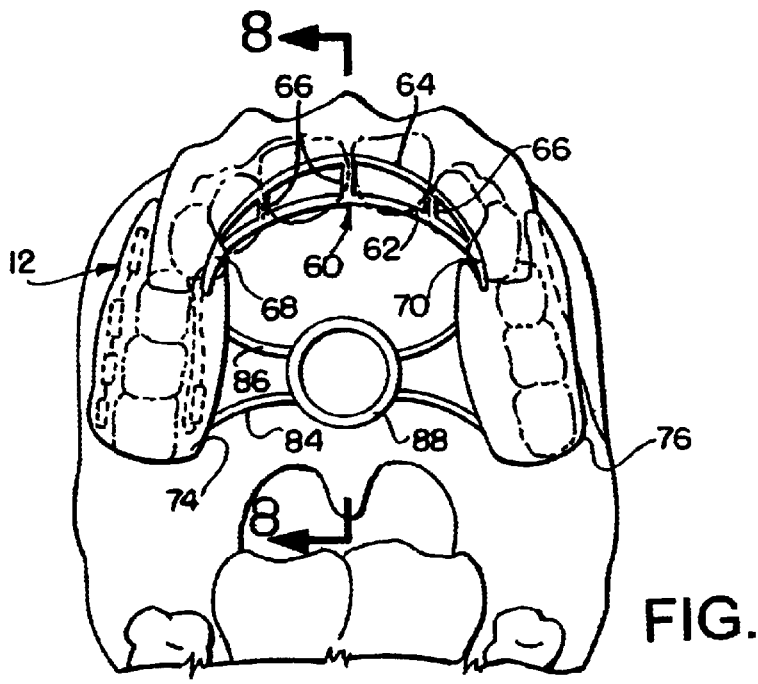
FIG. 7 is a partly cut away perspective illustration of a second embodiment of the present invention especially adapted to treat tongue thrusting.
Figure 8:
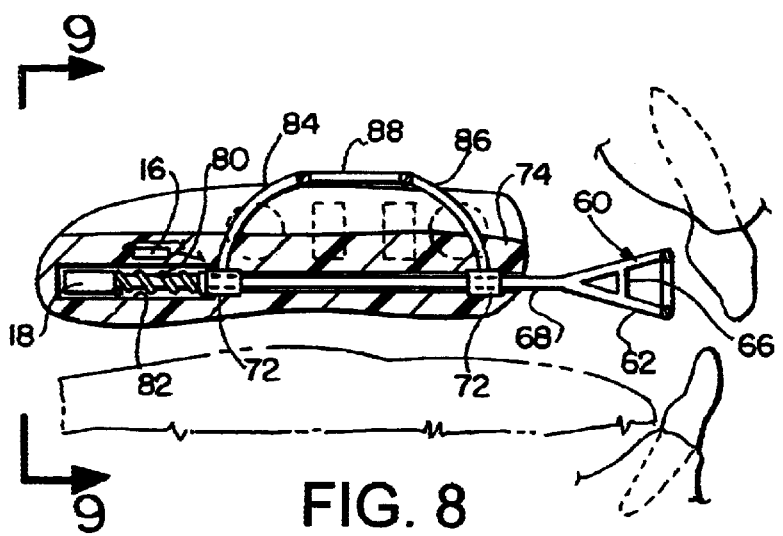
FIG. 8 is a side elevation view of the apparatus shown in situ in FIG. 7.
Figure 9:
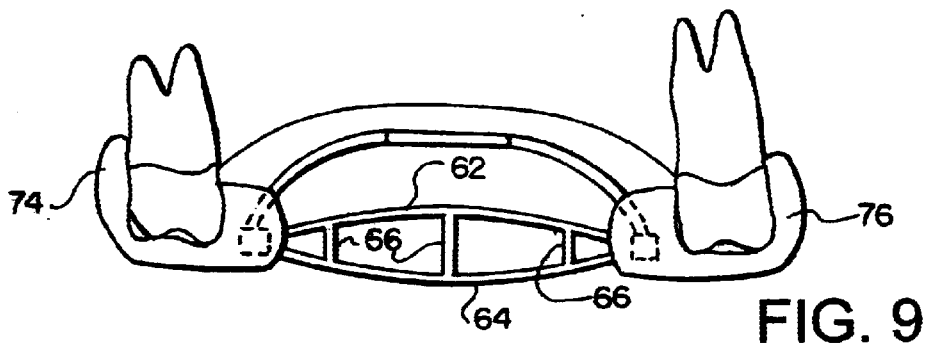
FIG. 9 is a view generally looking in the direction of arrows 9—9 of FIG. 8.

A further embodiment of the present invention is illustrated in FIGS. 7–9. Here the purpose is to treat tongue thrusting. Persistent tongue thrusting can result in moving teeth out of their desired alignment. In this case the relative position between the tongue and the incisors is what is being sensed. To achieve this a U-shaped cage 60 is fashioned out of a suitable metal or plastic. The cage 60 includes an upper and lower U-shaped horizontal band 62 and 64, respectively, interconnected by three vertical braces 66. The U-shaped members 62 and 64 merge into rods 68 and 70 which extend rearwardly from about the first or second premolar.

The rods 68 and 70 slide in bushings 72 (FIG. 8) which are embedded in polymeric housings 74 and 76. A magnet 18 is mounted to the rearmost end of the rod 68 and a reed switch 16 is embedded in the housing. A spring 80 biases the cage 60 rearwardly and the magnet 18 away from the reed switch 16. The spring 80 extends between one of the bushings 72 and the magnet 18. The housing 74 is formed with an appropriate internal cavity 82 which accommodates the movement of the rod 68, spring 80 and magnet 18.

When the tongue presses toward the inside of the front teeth, the cage 60 is moved forward, taking with it the magnet 18. This in turn brings the magnet into alignment with the reed switch 16 which is part of the circuit 12. This circuitry is essentially similar to that illustrated in FIG. 3A for treating clenching in that a signal is produced when the tongue has been pressed forward too long. In addition, as described above the circuitry also includes clock and counter memories 19 and 21, respectively, and a readout 23 for monitoring the number of times and/or length of time that the cage is within a predetermined distance from the patient's front teeth and for displaying such information to the treating dentist or orthodontist.

The polymeric housing 74 forms a splint covering the rearmost three or four upper teeth. The bushings 72, spring 80, magnet 18, and reed switch 16 are mounted in its lingual side. The circuitry 12, except for the reed switch 16, is carried in the buccal side of the splint 74. The splints 74 and 76 may be interconnected by a plastic arch which conforms to the shape of the palate, or as shown in the drawings, by a pair of wires 84, 86 and interconnecting ring 88.

The splint arrangement shown in FIG. 7 may be also used with the type of circuitry intended to treat clenching or in the alternative an open bite. In this case the upper band 42 (FIG. 2) would be eliminated while the lower band 40 would be retained to mount the magnet 18. Whether the splints 74 and 76 (FIG. 7) are used to secure the circuitry or an orthodontic band (e.g., 42, FIG. 2) depends on individual morphology and/or conditions present in the particular patient.

In some circumstances it might be useful to have a signal generated both when the tongue is thrust forward and when the jaw is slackened. In this case the polymeric splint 76 could contain circuitry like that discussed in connection with FIGS. 1–3A and an additional magnet would be attached to a mandibular tooth to actuate the circuitry. Such an arrangement could provide one signal when the tongue was thrust forward and a different and independent signal when the jaw has been excessively open. Again as described above, the circuitry 12 contains the necessary memory blocks in order to record the appropriate information for later retrieval by the treating dentist or orthodontist.

Once the patient has learned to keep his or her jaw tight and tongue relaxed, conventional orthodontia may be used to pull the teeth into proper alignment with the confidence that bad muscle habits will not undo what the orthodontia can achieve. As a further and optional feature, the circuit 12 (FIGS. 3A and 7) may include a memory and readout device 90. This device would record the patient's progress by measuring the number of times the tone generator 32 was actuated and for how long. The circuit 12 also includes means for permitting the dentist to read the stored information and displaying it, for example, on a computer screen or a computer controlled printer.

The connection between the memory and readout device 90 and the dentist's computer could be a direct electrical connection through a jack in the device 90 (shown schematically at 91) or it could be an inductive or capacitive connection. Such memories and readout devices are well known in the medical electronics field and are used extensively in cardiac pacemakers. If the circuit 12 is made with the memory and readout device 90, it is contemplated that it be integrated with the other circuit elements into a single integrated circuit.

In addition, the memories contained within the circuitry of the present invention can record a wide variety of data. For example, instead of the counter memory recording the number of times a specified condition occurs, the clock and counter memories 19 and 21, respectively, can be converted into memory for recording and tracking the temperature of the dental appliance above a predetermined threshold over any given time interval. This permits a treating dentist or orthodontist to determine if the patient is wearing his/her dental appliance as prescribed.

Figure 3B:
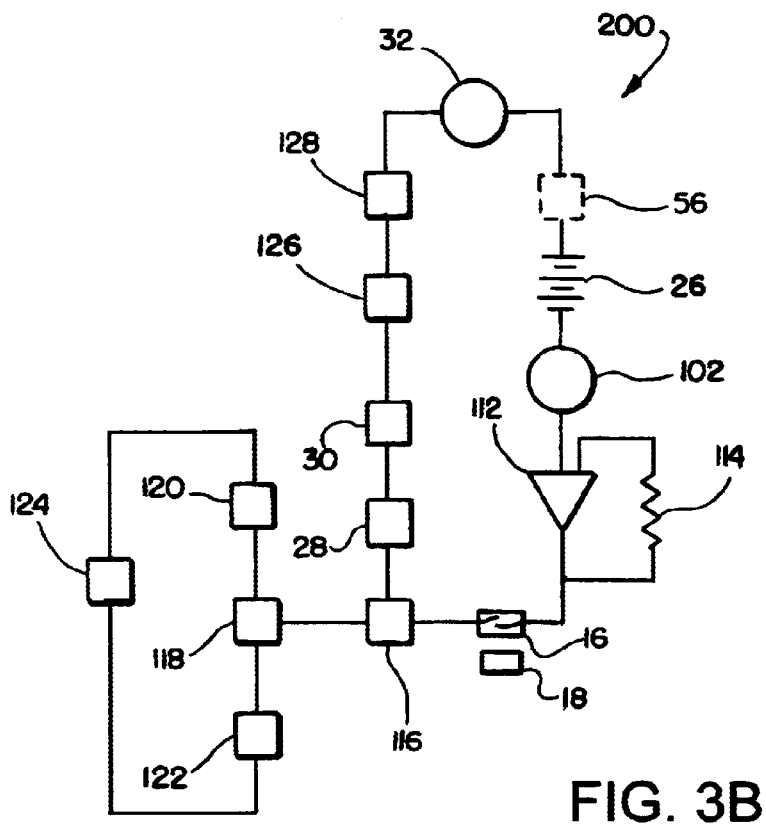
FIG. 3B is a schematic illustration of another embodiment of a circuit utilized in the present invention.

Another embodiment of circuitry for use in the present invention is shown in FIG. 3B. The circuit shown in FIG. 3B can, with any of the above described modifications, be used in any or all of the embodiments described above.

As seen in FIG. 3B, circuit 200 contains a battery 26 which is connected to a conductive rubber transducer 102 which acts as a force transducer and permits the measurement of a patient's bite forces. The rubber transducer 102 is connected to an amplifier 112 which has a feed back loop 114. The amplifier 112 is also connected to a reed switch 16 which is closed by a magnet 18. In one embodiment, circuit 200 only measures a patient's bite forces when the reed switch 16 is closed.

However, the circuit 200 may be configured in order to constantly monitor a patient's bite forces by deletion of the reed switch 16 and the magnet 18.

The amount of voltage generated by the circuit 200 is directly proportional to the amount of bite force exerted on the rubber transducer 102. The feed back loop 114 acts to prevent a voltage spike from damaging the circuit 200. The reed switch 18 is connected to a voltage detector 116 which measures the amount transmitted by the battery 26 and the amplifier 112 when the reed switch 16 is closed due to the proximity of the magnet 18.

Voltage detector 116 is further connected to a time delay circuit 28, and after a predetermined length of time, power is then passed to an oscillator 30 and from the oscillator 30 to a one shot 126 and then to a signal generator 128. Voltage is then passed from the signal generator 128 to a piezoelectric transducer 32 to alert the patient that his or her bite forces exceed a predetermined amount. In the case where the reed switch 16 and the magnet 18 are present the circuit 200 can also monitor whether or not and for how long a patient is clenching in the manner described above with regard to circuit 12.

The one shot 126 is, in one embodiment, a twenty (20) second one shot. Once the frequency generated by the oscillator 30 exceeds, for example, a predetermined level the one shot 126 is activated and moves into a second state which in turn activates the signal generator 128 so as to signal the patient that he or she is either clenching, exceeding a predetermined bite force, or both depending upon the signal generated by the signal generator 128. Once the one shot returns to its initial state, it ceases to signal to the patient. In this connection, the patient signaling device, being piezo electric, may generate an audible signal or merely a vibration that the patient can feel. Alternatively, any device which generates a recognizable sensation may be used, including a mild electric shock or a slight temperature change.

The one shot 126 stays in this second state for 20 seconds (i.e., a twenty second one shot) irrespective of the input from the oscillator. After the 20 seconds has elapsed the one shot will return to its initial state so long as the frequency from the oscillator does not meet the criteria set for switching the one shot into its second state.

Furthermore, as can be seen in FIG. 3B, the voltage detector 116 is also connected to a memory readout controller 118. The memory readout controller 118 is further connected to memories 120 and 122. The memories 120 and 122, in conjunction with the memory readout controller 118, record the bite force levels and the number of clenching events, respectively. Alternatively, the memories 120 and 122 can record other events or data such as temperature, position data, tongue thrusting events, etc. as described above with regard to clock and counter memories 19 and 21.

In addition, the circuit 200 includes a readout 124. If the device is only being used at night, the memories 120 and 122 can be permanently and directly connected to a readout 124. Alternatively, the readout 124 can be detachable and is activated when brought into contact with connectors on the circuit 200 (FIG. 10). In one embodiment, the readout 124 will be a conventional LCD display with its own power supply. All of these circuit elements are conventional. It is contemplated that in practice the circuit elements 28, 30, 112, 114, 116, 118, 120 and 122 will be formed in a single integrated circuit.

Alternatively, readout 124 can be similar in nature to readout 23 as described above.

The strength of the magnetic field surrounding the magnet 18 and its position relative to the reed switch 16 determines when the reed switch will close for treating clenching and cause a clenching incident to be recorded in the memory 122. The magnet 18 should be positioned so that when the teeth 22 and 24 come into contact the magnetic field at the reed switch 16 is just sufficient to close the switch. This is accomplished either by proper selection of the magnet's size or field strength or by positioning the magnet 18 relative to the reed switch 16.

For treatments which involve teaching the patient to hold his or her jaw closed, the magnet 18 might be such as to actuate the reed switch when teeth 22 and 24 are close to each other but not yet touching. For such treatments, the memory 122 can be configured to record the amount of time when teeth 22 and 24 are in contact with one another and/or the amount of time when teeth 22 and 24 are more than a predetermined distance apart. Again the information stored in memories 122 can be retrieved by either of the above described readout devices.

In another embodiment, the normally closed reed switch can be eliminated in favor of a different portion of the circuit 200 which is designed to function like a normally closed reed switch.

The time delay circuit 28 provides an adjustable time delay of between zero and about twenty seconds. This delay allows the patient to talk, eat, and swallow, all of which require contact between mandibular and maxillary teeth. The length of the time delay may be made variable. This can be done in a number of ways. Either a potentiometer can be used so that the resistance in an R-C circuit may be varied, or electronic components (either resistors or capacitors) could be removed or added to the circuit to achieve the same result. The same result could be obtained digitally with a clock and counter. The length of time would be varied by varying the length of the count. Again, such a circuit is conventional.

As discussed above, circuit 200 can be modified in the same manner as circuit 12 in order to allow for its use in determining any of the occurrences or conditions discussed above in connection with circuit 12.

Thus, it is clear that the present invention provides a new approach to treating both clenching, open bite/tongue thrusting and retrognathia problems. The electronic circuitry 12 or 200 may be attached to the upper teeth as in FIGS. 2 and 7 to sense the proximity of the lower teeth and to signal the patient when the jaw or tongue are in an undesirable position. For patients who clench, the circuitry 12 or 200 senses a closed jaw, and when the jaw has been held closed too long, a signal sounds alerting the patient to relax his or her jaw muscles. With open bite patients the circuitry 12 is arranged to signal the patient when the jaw has been open too long, and in the embodiment of FIGS. 7–9 the patient is signaled when his or her tongue is being pressed against the back sides of the front teeth. By providing a signal to the patient at the appropriate time, the patient can modify his or her behavior so that the cause of the patient's problem can be treated rather than merely the dental symptoms. Additionally, by providing data concerning the occurrence and duration of certain conditions in the mouth, the treating dentist or orthodontist is better able to determine what if any progress has been made and therefore recommend what further treatment, if any, is necessary. Also this information can be used to gather objective diagnostic data in order to determine a course of treatment.

What is claimed is:

1. An intraoral appliance comprising:
    proximity detector means for sensing the relative position of body parts in the oral cavity,
    signal means connected with the detector for signaling when body parts in the oral cavity are in an undesirable position, and
    memory means and display means for storing and displaying information about the relative position of body parts in the oral cavity when the body parts in the oral cavity meet predetermined criteria;
    the signal means including time delay means for delaying a signal until the body parts have been in an undesirable position for a predetermined length of time,
    the display means being located within the oral cavity.

2. The appliance of claim 1 wherein the time delay means includes means for selecting the length of the time delay.

3. The appliance of claim 1 wherein the proximity detector means includes a reed switch and magnet for actuating the reed switch.

4. The appliance of claim 1 wherein the proximity detector means and the signal means are embedded in synthetic material.

5. The appliance of claim 4 wherein the material is a polymeric material.

6. The appliance of claim 1 wherein the proximity detector means includes a first part adapted to be connected with a maxillary tooth and a second part adapted to be connected with a mandibular tooth.

7. The appliance of claim 6 wherein at least one of the parts is readily removable.

8. The appliance of claim 1 including cage means adapted to be connected with proximity detector means for sensing the position of the tongue.

9. The appliance of claim 8 wherein the cage means is forwardly movable in response to forward movement of the tongue.

10. The appliance of claim 9 including biasing means for urging the cage rearwardly.

11. The appliance of claim 10 wherein the biasing means includes a spring.

12. The appliance of claim 9 including splint means for engaging teeth, the splint means containing the signal means, the cage means being forwardly and rearwardly movable with respect to the splint means.

13. The appliance of claim 1 wherein the signal means includes means for generating a signal that is audible to the appliance wearer.

14. The appliance of claim 1 wherein the signal means signals when mandibular and maxillary teeth have been in contact longer than the predetermined length of time.

15. The appliance of claim 1 wherein the signal means signals when mandibular and maxillary teeth have separated longer than a predetermined length of time.

16. The appliance of claim 1 wherein the display means is an LCD display incorporated into the intraoral appliance.

17. The appliance of claim 1 wherein the display means includes a sound generator.

18. The appliance of claim 17 wherein the sound generator interacts with a computer to generate a visual display.

19. The appliance of claim 1 wherein the memory means comprises a clock memory for recording time based information and a counter memory for recording numerical data.

20. The appliance of claim 19 further comprising a bite force memory for recording bite forces which exceed a predetermined threshold.

21. An intraoral appliance for comprising a memory means and display means for storing and displaying temperature information that meets predetermined criteria,
    the display means being located within the oral cavity.

22. The appliance of claim 21 wherein the intraoral appliance is a retainer.

23. The appliance of claim 21 wherein the intraoral appliance is a splint.

24. The appliance of claim 21 wherein the intraoral appliance is a mouth guard.

25. A method of treating a patient comprising the steps of
    sensing when body parts in the oral cavity have been in an undesirable position for longer than a predetermined time,
    distinguishing between momentary and prolonged undesirable positioning of the body parts,
    signaling the patient in response to prolonged undesirable positioning of the body parts,
    recording the frequency and amount of time the patient's body parts in the oral cavity are in an undesirable position for longer than a predetermined time and
    displaying information concerning the frequency and amount of time the patient's body parts in the oral cavity are in an undesirable position on a display within the patient's oral cavity;
    whereby the patient may voluntarily move the body parts to a more favorable position.

26. An intraoral appliance comprising
    proximity detector means for sensing the relative position of body parts in the oral cavity,
    signal means connected with the detector for signaling when body parts in the oral cavity are in an undesirable position,
    cage means connected with the proximity detector means for sensing the position of the tongue, the cage means being forwardly movable in response to forward movement of the tongue,
    biasing means including a spring for urging the cage rearwardly, splint means for engaging teeth, and memory means and display means within the oral cavity for storing and displaying information about the relative position of body parts in the oral cavity;

the splint means containing the signal means, the cage means being forwardly and rearwardly movable with respect to the splint means, and the splint means including two portions, each adapted to engage teeth on a different side of the oral cavity.

27. The appliance of claim 26 including bridge means connecting the two portions of the splint means.

28. The appliance of claim 26 wherein the cage means includes a U-shaped wire contoured to follow the inside perimeter of the maxillary or mandibular teeth.

29. The appliance of claim 28 including biasing means for urging the cage means rearwardly, the proximity detector means detecting movement of the cage means forward against the bias of the biasing means.

30. The appliance of claim 26 wherein one of the portions of the bridge means contains signal means and proximity detector means adapted to sense the relative position of the first pair of body parts in the oral cavity and the other of the portions of the bridge means contains signal means and proximity detector means adapted to sense the relative position of a second pair of body parts in the oral cavity.

31. A method of treating a patient comprising the steps of placing a proximity sensing and signaling device entirely within the patient's oral cavity, sensing when body parts in the patient's oral cavity are in an undesirable position, signaling the patient whereby the patient, being aware of the undesirable proximity, may voluntarily move the body parts to a more favorable position, including signaling when the patient's tongue is pressed against the patient's incisors, signaling when a mandibular and a maxillar tooth have been spaced apart by more than a predetermined distance for more than a predetermined length of time, recording the frequency and amount of time the patient's body parts in the oral cavity are in an undesirable position for longer than a predetermined length of time, and displaying information concerning the frequency and amount of time the patient's body parts in the oral cavity are in an undesirable position on a display within the patient's oral cavity.

\* \* \* \* \*